United States Patent [19]

De Vries et al.

[11] 4,120,582
[45] Oct. 17, 1978

[54] LIGHT REFLECTIVITY AND TRANSMISSION TESTING APPARATUS AND METHOD

[75] Inventors: Martin De Vries; Harold A. Fitzgerald, II, both of Holland; Eldon J. Nyhof, Zeeland; James D. van Putten, Jr., Holland, all of Mich.

[73] Assignee: Donnelly Mirrors, Inc., Holland, Mich.

[21] Appl. No.: 736,251

[22] Filed: Oct. 27, 1976

[51] Int. Cl.² .................... G01N 21/48; G01N 21/22; G01J 1/04
[52] U.S. Cl. ..................................... 356/73; 356/236
[58] Field of Search ................ 356/73, 201, 209, 236; 250/228, 574

[56] References Cited

U.S. PATENT DOCUMENTS 3,746,869  7/1973  Lindstedt et al. ..................... 356/73

OTHER PUBLICATIONS

Sae, "Test Procedure for Determining Reflectivity of Rear View Mirrors," Sae V964a, Aug. 1974, (Revised).
Sketch of "Integrating Sphere Refrectometer," Manf. & Used by Assignee of Applicants.
Baumgartner; G. R., "A Light Sensitive Cell Refrectometer," G. E. Review, Nov. 1937, pp. 525-527.
Karrer; E., "Use of the Ulbright Sphere in Measuring Refrection & Transmission Factors," Sci. Papers of Bureau of Stand, #415, Aug. 10, 1921, pp. 216-225.

Primary Examiner—John K. Corbin
Assistant Examiner—Wm. H. Punter
Attorney, Agent, or Firm—Price, Heneveld, Huizenga & Cooper

[57] ABSTRACT

Apparatus and method for testing an optical element sample such as a mirror simultaneously and substantially instantaneously both for the total amount of light reflected from and the total amount of light transmitted by a predetermined area of that sample. The apparatus includes a pair of axially aligned light-integrating spheres between which is clamped the test sample so that no light enters or escapes from either sphere. A preferably optically regulated, substantially collimated beam of light is directed through one sphere against the test sample at an angle to the sphere axis. Silicon photovoltaic light sensitive detectors connected to amplified readout units indicate the total light reflectivity in one sphere and the total light transmission to the other sphere. The method includes directing a light beam against a test sample area at an angle other than normal to the surface of said sample area, simultaneously detecting the total amounts of reflected and transmitted light for the test sample area with light-integrating means, and indicating the detected total amounts of reflected and transmitted light.

29 Claims, 7 Drawing Figures

LIGHT REFLECTIVITY AND TRANSMISSION TESTING APPARATUS AND METHOD

BACKGROUND OF THE INVENTION

This invention relates to an apparatus and method for testing the reflectivity and transmission of light by various materials or objects and, more particularly, to the testing of the total light reflectivity and total light transmission of optical elements, and especially those intended for use by humans such as rearview mirrors for vehicles and the like.

In the manufacture of optical elements such as rear view mirrors and the like, it is preferable to test each mirror element to determine its optical qualities, namely, the amounts of an incident light beam it reflects and transmits. Various apparatuses and methods are known for conducting such testing. In one method, a light source provides a single beam of light which is split into a pair of identical light beams which are directed through separate test apparatus each of which includes either a standard or known sample or a test sample of a mirror or the like. Not only is such duplication of test apparatus expensive and often subject to error, but most such apparatuses require separate testing of reflectivity and transmission of light through the samples. Consequently, it is often difficult to assure that the same area of the test piece is being tested for reflectivity and transmission.

In other apparatuses, a standard sample and a test sample are tested alternately, one after the other by mounting them in appropriate holders and inserting them in a test apparatus. In such structures, it is usually necessary to test the standard sample immediately before or immediately after the test sample in order to determine an accurate and representation reading. Moreover, such structures have been subject to inaccuracies and have generally been quite complex. They also have required the separate testing of each sample for light reflectivity or transmission or the modification of the apparatus to obtain the separate values.

An additional problem with certain prior reflectivity and transmission testing methods has been the necessity of measuring either specular or diffuse reflection separately. The two types of reflection must then be added by electronic means or the like to obtain a proper readout. Further, it has often been difficult to obtain an indication of reflectivity and transmission equivalent to that of the photopic human eye response.

In the mass production of optical elements such as rear view mirrors for automobiles, the prior known structures and methods mentioned above have caused significant problems and delays in testing each optical element produced. A substantial need has therefore existed for a light reflectivity and transmission testing instrument or apparatus and method which enables the simultaneous testing of the total reflectivity, including both specular and diffuse reflection, as well as the total transmission of light of the identical area of an optical element in a manner similar to the response of the photopic human eye. A need has also existed for the capability of such testing on a successive, high production basis without having to modify the test apparatus to determine the desired, distinct values or to insert a standard test sample after each production sample is tested.

SUMMARY OF THE INVENTION

Accordingly, the present invention provides an apparatus and method for simultaneously and substantially instantaneously testing an optical element sample such as a rearview mirror for a vehicle so as to determine the amount of light reflected from a predetermined area of the sample as well as the total amount of light transmitted through that same area of the sample.

The testing apparatus includes first and second closed, hollow light-integrating means aligned along a common axis, each light-integrating means including a test aperture extending through one portion. The test apertures are aligned with and adjacent one another between the light-integrating means. Support means are provided for supporting a test sample such as a mirror tightly against and between the light-integrating means an immediately adjacent the test apertures. A light source is provided for directing a beam of light at an angle to the axis of the light-integrating means which angle is other than normal to the surface of the area of the test sample which is between the test apertures. The light beam is directed through the first integrating means, the test aperture in that first integrating means, and against the test sample such that is would pass through both test apertures and on into the second integrating means in the absence of a sample. Photo-detection means are included for detecting the total amount of reflected light in the first integrating means and the total amount of transmitted light in the second integrating means. Also included are means for separately indicating the total amounts of reflected and transmitted light respectively detected by the photo-detection means.

In the preferred embodiment of the apparatus, the integrating means are spheres having optically white, matte finished inside surfaces. One of the spheres is movable with respect to the other for clamping a test piece therebetween while light sealing means are provided to prevent the entry or escape of light into or from the individual spheres. Further, the indicating means include means for comparing the total amounts of reflected and transmitted light from the test sample to a known or predetermined standard value for each.

The method includes directing a beam of light against the surface of a predetermined area on one side of the test sample at an angle other than normal to that surface, simultaneously detecting the total amount of light reflected from and the total amount of light transmitted through the said area of the test sample with light-integrating means, and indicating the respective total amounts of reflected and transmitted light so detected.

The present apparatus and method provide numerous advantages over prior known testing structures and methods. The reflectivity and transmission values determined with the apparatus and method are total, not partial, with the reflectivity value including both specular and diffuse reflectivity therein. The apparatus and method are highly accurate and include fixed optical geometry which need not be changed for successive tests of successive optical element. The apparatus can be used to quickly and rapidly measure various sizes and thickness of optical element samples including concave, convex, and planar samples, first and second surface mirror samples, and rigid or flexible samples.

There is no need to adjust the apparatus after the testing of each successive optical element sample since the instrument merely requires one setting with a standard sample or the direct beam of light prior to the beginning of testing of production pieces. The instrument does not destroy or damage the test pieces and is not sensitive to nonuniform photo-detector surfaces thereby obviating the need for any diffusing screens within the light-integrating means. The instrument is not subject to polarization or image inversion problems and provides reflectivity and transmission values corrected for the normal photopic human eye response. The instrument is, therefore, excellent for testing mirrors to be used by humans such as in autos and other vehicles. The instrument also meets the Society of Automotive Engineer requirements and recommended practices for testing the optical qualtities of rear view mirrors.

In addition, no internal structure or shield within the light-integrating means is required because the instrument measures total reflectivity including both diffuse and specular reflectivity. The instrument does not leak light in or out and therefore can be used in either a light or dark environment. Also, the instrument is optically stable and preferably uses an optically regulated, collimated, light source powered by a constant current power supply which provides a beam of light including all visible wavelengths of light to increase the accuracy and reliability of the testing.

These and other objects, advantages, purposes and features of the invention will become more apparent from a study of the following description taken in conjunction with the drawings.

DESCRIPTION OF THE PREFERRED EMBODIMENTS

Testing Apparatus

Referring now to FIGS. 1–4 and 6, the light reflectivity and transmission testing apparatus 10 includes a base plate 12, a pair of upwardly and outwardly extending support arms 14 braced by triangular plates 16. Arms 14 support a light source support member 18 secured at their spaced, upper ends. Support 18 secures a light source and optical component housing 60 which provides an optically regulated, substantially collimated, beam of light which is directed downwardly through a pair of vertically aligned light-integrating spheres 20, 30 secured above base 12. As it will be more fully described hereinafter, the lower sphere 30 is vertically movable toward and away from upper sphere 20 so as to clamp therebetween an optical element test sample such as a mirror M to test that sample for total reflectivity and total transmission of the light beam simultaneously and substantially instantaneously.

Figures 1, 2, 3:
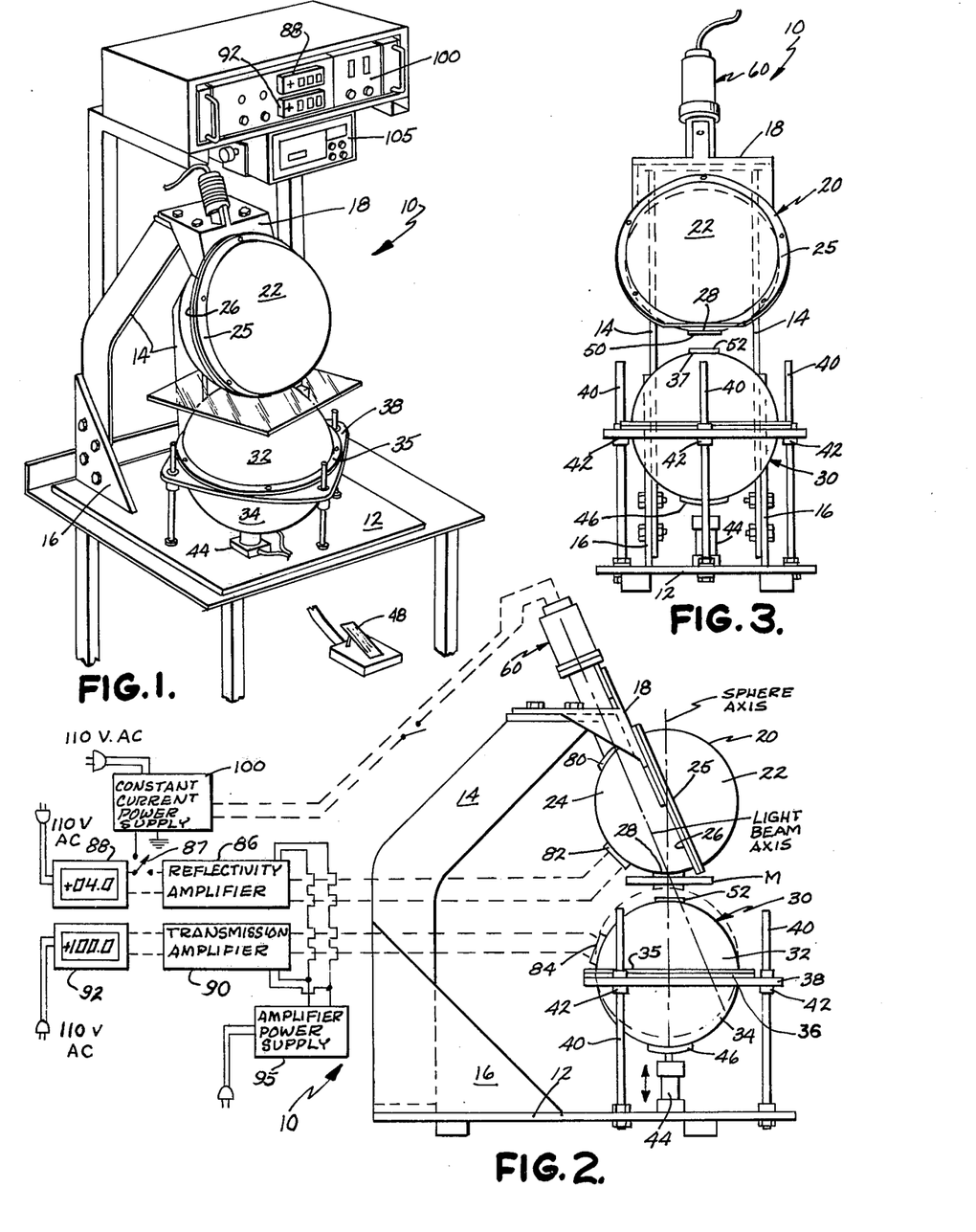
FIG. 1 is a perspective view of the total reflectivity and total transmission testing apparatus for optical elements.
FIG. 2 is a side elevation of the testing apparatus shown in FIG. 1 illustrating the two positions of the movable lower light-integrating sphere as well as a schematic illustration of the amplifying readout and power supply circuitry of the apparatus.
FIG. 3 is a front elevation of the testing apparatus shown in FIGS. 1 and 2.
Figures 4, 5, 6, 7:
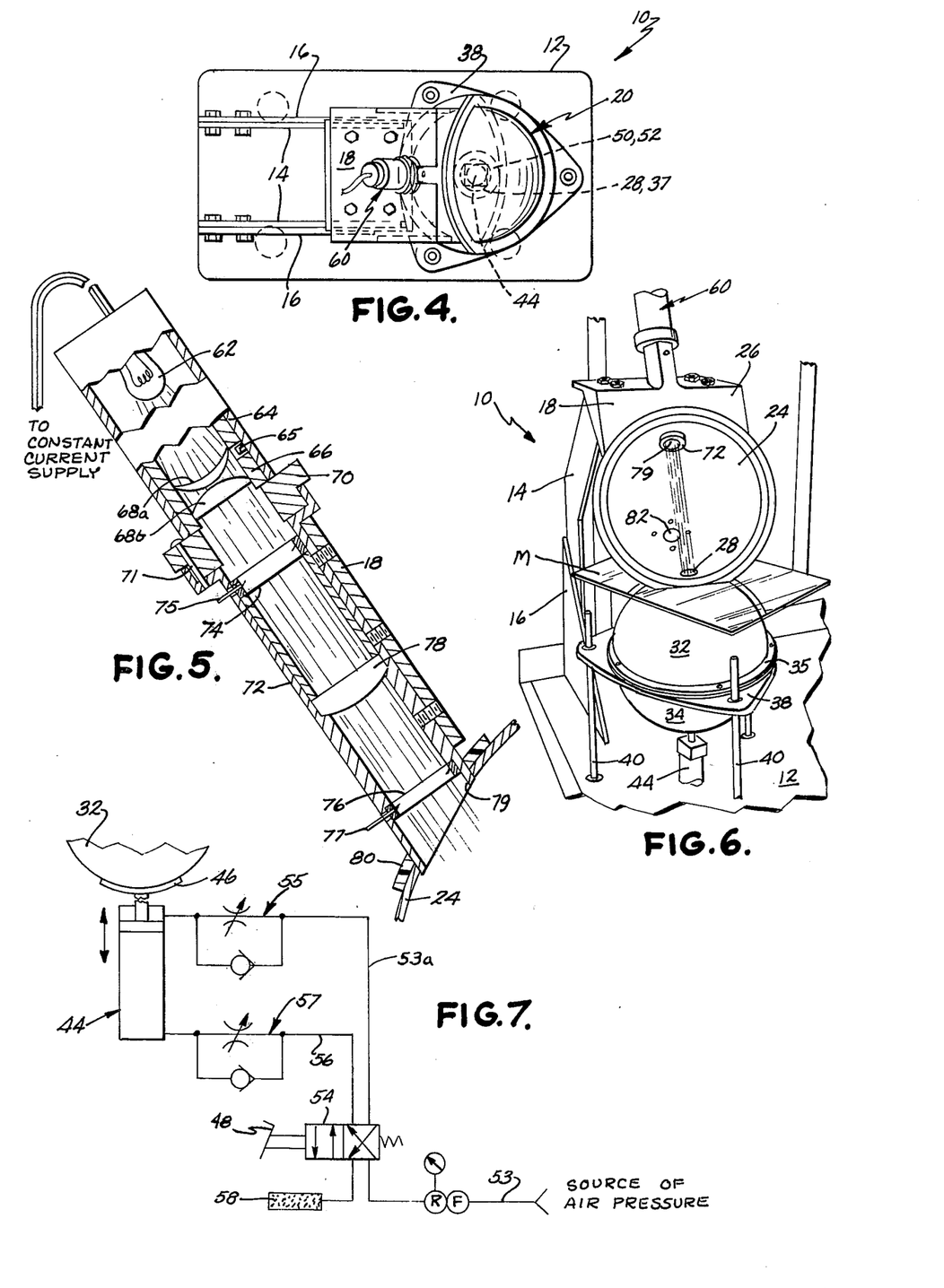
FIG. 4 is a plan view of the testing apparatus shown in FIGS. 1–3.
FIG. 5 is a fragmentary, enlarged side elevation with portions broken away illustrating the light source and optical components for providing a collimated beam of white light in the invention.
FIG. 6 is a fragmentary, perspective view of the testing apparatus shown in FIGS. 1–4 with the front half of the upper light-integrating sphere removed to show the interior thereof.
FIG. 7 is a schematic illustration of the pneumatic circuitry for controlling the movement of the lower light-integrating sphere toward and away from the upper sphere.

As is best seen in FIGS. 1, 2, and 6, each of the spheres 20, 30 is a closed, hollow, molded plastic, spherical shell or housing formed in two hemispheres 22, 24 and 32, 34 respectively. These spheres have equivalent diameters to ensure equal accuracy in measuring both total reflection and total transmission of light. Each hemisphere includes a circumferential flange 25, 26, 35 or 36 which meets and mates with a like flange of the other hemisphere at an equator of each sphere for securing the two halves together. The inside surface of each sphere and hemisphere is smooth, even and coated with an optically white material such as barium sulfide (BaSo$_4$) in a matte finish. The optically white, matte surface provides a neutral, diffuse, equal reflection for all visible wavelengths of light. The light-integrating sphere is a device conventionally known in the science of optics which internally reflects and averages light present therewithin to provide a uniform light level throughout. Other closed, hollow light-integrating devices could also be used in this invention. It is necessary that these integrating means be closed in order to exclude ambient, environmental light from around the instrument and in order to prevent the escape of any reflected or transmitted light being detected.

Hemisphere 24 of upper sphere 20 is secured to the arcuate, downwardly extending flange of support member 18 such that is opens outwardly and upwardly (FIG. 6). A circular aperture 28 is provided in one portion of the circumference of hemisphere 24 such that when the hemisphere is mounted on the support 18, aperture 28 is oriented vertically. Hemisphere 22 is removably secured to flange 26 via flange 25 so that one may gain access to the interior of the sphere 20 for maintenance or other purposes. Hemisphere 32 of sphere 30 includes a circular aperture 37 (FIGS. 2 and 3) similar to aperture 28 which is axially aligned with aperture 28 of the upper sphere along the sphere axis such that the apertures are immediately adjacent one another between the spheres.

Lower sphere 30 is mounted directly below upper sphere 20 and in axial alignment with the spherical axis which extends vertically through aperture 28 (FIG. 2). However, sphere 30 is mounted for controlled, vertical sliding movement on a generally triangular retainer 38 including a circular aperture therethrough receiving the lower hemisphere 34 of sphere 30. A trio of vertically extending guide posts 40 are secured to base 12 and extend upwardly through guide bushings 42 mounted in corresponding apertures in retainer 38. One guide post is located at each corner of the triangular retainer. Beneath sphere 30 and specifically hemisphere 34, is mounted a small, pneumatic cylinder 44 which includes a movable piston connected to lower hemisphere 34 of sphere 30 via a partially spherical plate 46 (FIGS. 1–3, 6 and 7). The piston is controlled pneumatically to raise and lower sphere 30 and thus vary the spacing between the spheres for insertion and support of a test sample M (solid and phantom lines in FIG. 2) as will be described more fully hereinafter. The maximum thickness of a test sample M which can be inserted between spheres 20, 30 is the largest thickness which allows passage of the beam of light from source 60 through apertures 28, 37 and into lower sphere 30. In the preferred embodiment, this maximum thickness is about 0.75 to 1.00 inches.

As annular, resilient, black, opaque, neoprene foam rubber pad or ring 50, 52 is glued to otherwise secured about each aperture 28, 37 respectively to serve both as a resilient support for the optical element test samples when clamped between the two spheres as well as a light seal to prevent ambient, environment light from entering either sphere an any reflected or transmitted light present within the respective spheres from escaping before being detected and measured. Light seals 50, 52 therefore increase the accuracy and reliability of the apparatus and prevent damage to the test samples.

Control of the vertical movement of lower sphere 30 toward and away from upper sphere 20 is obtained via foot pedal 48 and the pneumatic control system shown in FIG. 7. Air pressure from a suitable source, such as in the building where the instrument is installed, enters air line 53 and passes through an appropriate filter and regulator to one side of a pneumatic valve 54 biased so as to allow air pressure to hold the piston within fluid cylinder 44, and thus the lower sphere 30, in its up or raised position against the upper sphere 20. Maintenance of the spheres against one anotheer when not in use helps keep dust, dirt and the like out of the sphere interiors. In such case, air pressure continues through valve 54, line 56 and adjustable flow control valving 57 into the lower portion of cylinder 44. The upper portion of the cylinder over the piston is open to exhaust and muffler 58 through another passage of valve 54 and air line 53a.

To lower the cylinder for insertion of a test piece between the spheres, foot pedal 48 is depressed shifting valve 54 to the right and allowing line air pressure to travel through lines 53 and 53a and lower the piston in cylinder 44. In such case, air in line 56 and below piston 44 is exhausted through the opposite side of the valve and muffler 58. An adjustable fluid control valve 55 is also included in line 53a. Valves 55 and 57 allow the piston within cylinder 44 to travel at a fast rate of speed until the ends of its strokes are reached.

Referring now to FIGS. 2 and 5, the light source and optical components housing 60 includes an incandescent tungsten filament light bulb 62 connected by appropriate circuitry to power supply 100 (FIGS. 1 and 2) which provides a quantitively constant source and supply of electrical current. The filament operates at a nominal color temperature of 2854° Kelvin and provides a spectral response substantially equal to that classed by the Commission Internationale de L'Eclairage (CIE) as the standard illuminant A. The constant current supply provides a reasonably stable light emission from the filament since the amount of light from a filament is proportional to the amount of current passing therethrough. A tungsten filament is used to provide a mixture of all wavelengths visible to the human eye.

Light bulb 62 is mounted at the end of a cylindrical housing 64 telescoped over a cylindrical lens mounting cylinder 66 including a positive-meniscus lens 68a and a plano-convex 68b which cause the light to converge into a beam with an adjustable focus. Focusing of the light into the collimated beam is obtained by rotating housing 64 which includes a projection 65 extending into a helical groove in housing 66 to move housing 64 and thus bulb 62, toward and away from lenses 68a, 68b. Housing 64, including the bulb and lenses, is secured to a cylindrical, flanged housing 72 via a flanged collar 70 and securing bolts 71. Cylindrical housing 72 is axially aligned with housing 64 and lenses 68a, 68b and includes a pair of adjustable aperture irises 74, 76 for controlling the diameter of the beam of light. One iris is mounted at either end of the housing 72 while another plano-convex lens 78 is secured intermediate the ends of housing 72. Housing 72 ends with a beam entrance aperture 79. Lens 78 further focuses the light into a collimated beam. The aperture sizes of irises 74, 76 are adjusted by radially extending levers 75, 77 which are moved circumferentially to open or close the movable elements of the iris.

Light source and optical components housing 60 is secured to support 18 such that housing 72 extends through an aperture in the circumference of hemisphere 24 of upper sphere 20 (FIGS. 5 and 6). A foam light seal 80 (FIGS. 2 and 5) is provided around the junction between housing 72 and sphere 24. The axis of the collimated beam of light provided by source 60 (FIG. 2) is 25° plus of minus 5° from the vertical which corresponds to the axis of alignment of the spheres 20, 30. This angle is also other than normal to the surface of the area of the test sample exposed within the apertures 28, 37 in order to prevent reflection of a major portion of the light back out of the aperture through which the light source is inserted. The beam of light is aligned, focused and directed so that it passes through aligned apertures 28, 37 as shown in FIG. 2 when the lower sphere is in its raised, clamping position.

When an optical element test sample is positioned between the spheres 20, 30 and the collimated beam of light from source 60 is directed thereagainst as shown in FIG. 2, it strikes the test sample and is divided into two major beams including a reflected beam and a transmitted beam. The reflected beam strikes the optically white interior surface of the upper sphere 20 and is reflected off the walls repeatedly in all directions and on all areas. The total amount of light reflected by the test sample M is reflected into the upper sphere 20 including both specular and diffused reflection. An average light level or intensity in the upper sphere is thereby created which can be detected or sensed. The second or transmitted beam which passes through the test sample reflects repeatedly off the optically white interior of the lower sphere 30 to provide an average, transmitted beam intensity which also can be sensed and detected.

Silicon, photo-voltaic light sensitive cells or detectors 82, 84 are each mounted through an aperture in each sphere 20, 30 so as to sense and detect the total amount of reflected and transmitted light present in the upper and lower spheres, respectively. The sensing surface of each detector is substantially flush with the interior of its sphere. Photo detector 82, 84 are sensitive to the light level in their respective spheres and transform that light level into electrical energy proportional to the level of light. These photo detectors are preferably mounted behind the position of the light beam from light source 60 so as not to be directly in line with direct reflection or transmission of the main or principal beam as shown in FIG. 2. No diffusing screens or shields are mounted over or in front of the photo detectors 82, 84 since apparatus 10 is used to test total reflectivity including specular and diffuse reflection in sphere 20 and total transmission in sphere 20. A preferred photodetector unit is the silicon solar cell, Model No. 21S51, manufactured by Vactec, Inc. of Maryland Heights, Missouri.

Photo detectors 82, 84 are connected electrically to an indicating system which provides a readout of the light levels in spheres 20 and 30 based on the electrical energy provided by the photo detectors. The indicating system includes a reflectivity amplifier 86 connected to a digital readout unit 88 as well as a transmission amplifier 90 connected to a digital readout unit 92. Power is supplied for the amplifiers from a constant voltage power supply 95 connected to a 110 volt alternating current line source.. Readout units 88, 92 are separately connected to a line source of 110 volt alternating current electricity. Light source 60 is powered by a power supply 100 which is of the adjustable type which supplies a constant current supply. The power supply 100 is in turn connected to a 110 volt, alternating current, line electrical source. If desired, a printer 105 (FIG. 1) may be connected to readout units 88, 92 to provide a written record of the test.

Amplifiers 86 and 90 may be of any conventional type which provide a linear response as well as high gain and low noise to obtain the most accurate results with the present instrument. These amplifiers are adjustable so that they may indicate on the readout units 88, 92 the percentage of reflectivity and transmission. The readout units therefore provide a visual comparison readout in a percentage reflectivity or transmission relative to a standard value.

In the preferred embodiment of apparatus 10, the entire system is designed to provide readings as close as possible to those which would be seen by the normal photopic human eye. Detectors 82, 84 are sensitive to and have an electrical output directly proportional to the spectral wavelengths visible to the normal photopic human eye. The detectors are matched to the amplifiers and readout units as well as the color temperature of bulb 62, which is preferably CIE standard illuminant A, 2854° Kelvin, so that a readout value giving the total reflected or transmitted light in the range of wavelengths visible to the photopic human eye is provided. This is especially important for use of the apparatus 10 to test the reflectivity and transmission of optical elements intended for use by humans. These would include rear view mirrors for vehicles and the like. Further, to maintain a high degree of accuracy, the internal wall areas of spheres 20, 30 must be large with respect to the sum of the aperture and detector areas of the sphere interiors, i.e., the sensitive area of the detector 82 or 84, the test aperture 28 or 37, and the light beam entrance aperture 79. In the preferred embodiment, spheres 20, 30 have inside diameters of approximately 8.91 inches, detectors 82, 84 have a diameter of approximately 0.81 inches, apertures 28, 37 have diameters of approximately 1.18 inches, and beam entrance aperture 79 has a diameter of approximately 1.58 inches. The actual sphere, aperture and detector sizes are chosen to achieve a desired per cent accuracy for the tests conducted with the instrument using the following formula:

$$\frac{100 \text{ (total areas of apertures and detector in sphere)}}{\text{(total inside surface area of sphere)}} \leq 2 \begin{pmatrix} \text{per cent of} \\ \text{accuracy to} \\ \text{be achieved} \end{pmatrix}$$

With the sizes mentioned above, the percent accuracy of the instrument is ± ½% when the reflectivity standards used in calibration of the instrument are themselves accurate to ± 0.3%.

To operate the testing apparatus, the apparatus is first calibrated so that the readouts provided on units 88, 92 are expressed as a percentage of complete reflectivity and complete transmission and are referenced to known values for reflectivity and transmission. To calibrate for reflectivity, a known standard sample having a known, optimum reflectivity (typically 75%) value is inserted between spheres 20 and 30 and illuminated by light source 60. The amount of reflected light present in the upper sphere 20 is sensed by detector 82 and amplified by amplifier 86. Switch 87 is switched to connect power supply 100 to readout meter 88 and the current to bulb 62 is adjusted so that readout unit 88 reads a voltage value, typically 6.5 v, which is equivalent to the voltage necessary to provide a nominal color temperature of 2854° Kelvin, i.e., CIE illuminant A, with the tungsten filament. Next, switch 87 is switched to connect amplifier 86 and detector 82 to readout unit 88. A low-reflective member (typically reflecting 6.6% of an incident beam) is inserted between the spheres. The zero adjustment or low current adjustment of amplifier 86 is then adjusted so that readout unit 86 reads the known low reflectivity value, i.e., typically 6.6%. These adjustments are preferably repeated four or five times before beginning any testing to ensure accuracy. Thereafter, when test samples which generally will have reflective coatings which reflect less than the optimum, known amount of light are tested with the apparatus, readout unit 88 will detect and read the total reflected light from such samples as a percentage of the complete, total 100% reflection of light set with the standard sample.

To calibrate for transmission values, all samples are removed, lower sphere 30 raised such that light seals 50, 52 are tightly engaged with one another, and a beam of light from source 60 is projected directly into the lower sphere. Detector 84 senses this amount of light which is amplified by amplifier 90, and the gain adjustment of amplifier 90 is adjusted so that readout unit 92 reads "100.0". Next, the opaque, nontransmitting sample is inserted between the spheres and the zero or low current adjustment of amplifier 90 is adjusted so that readout unit 92 reads 0.00. These adjustments are also preferably repeated for accuracy. Thereafter, when test samples are inserted between the spheres and a lesser amount of light is transmitted because of the obstruction by the sample, the amount of transmitted light will be read as a percentage of the known, unimpeded light beam.

DESCRIPTION OF THE PREFERRED METHOD

The preferred method for testing for total reflectivity and transmission light values begins with the calibration of the testing instrument 10 as described above to obtain known values on the readout units to which the values for the test samples will be compared. Foot pedal 48 is depressed to lower sphere 30 for insertion of a test sample M between the upper and lower spheres 20, 30 and the foot pedal 48 is released to raise the lower sphere such that the sample is clamped tightly between light seals 50, 52 and spheres 20, 30. The surfaces of the test sample are substantially normal to the axis of alignment of the spheres in the area of the apertures 28, 37. Light source 60 is switched on and provides an optically regulated, collimated beam of light which is directed against the upper surface of the test sample at an angle of 25° plus or minus 5° as mentioned above. This is an acute angle to the vertical and is other than normal to the surface of the sample so that light will not be reflected out of the light source opening which would thereby provide an inaccurate reading for total reflectivity.

As mentioned above, the beam is split into reflected and transmitted portions which remain in the upper sphere and pass into the lower sphere, respectively. The total amount of reflected light in the upper sphere as well as the total amount of transmitted light in the lower sphere is then detected by first gathering or collecting and averaging the respective amounts of light and secondly sensing those amounts. Light is reflected by the optically white interiors of the upper light-integrating sphere 20 and the lower light-integrating sphere 30 to provide an average light level within each sphere. As mentioned above, closed, hollow, light-integrating devices other than the spheres described herein may be used as long as they can exclude ambient, environmental light and prevent the escape of reflected and transmitted light from the interiors thereof. It is also important that a separate light-integrating device be provided for collecting and averaging separately the total amounts of reflected and transmitted light from the test sample.

The amount of reflected and transmitted light is then simultaneously and substantially instantaneously sensed in each sphere, respectively, preferably with a silicon, photo-voltaic, light-sensitive cell such as shown at 82, 84 located in each sphere. These cells convert the amount of light present into electrical energy which is thereafter amplified by amplifiers 86, 90 and read out as a percentage of absolute reflectivity and transmission values previously calibrated on amplifier units 86, 90. The photo-voltaic sensors are sensitive to the wavelengths visible to the normal photopic eye and are matched and coupled to the amplifying and readout units so that those units indicate the total amounts of light present which is visible to the photopic human eye. Also, the color temperature of the light source 60 is designed to produce constant CIE standard illuminant A light emission which includes all wavelengths visible by a human. The system is thus matched for a response simulating that of a human eye. This enables effective and accurate testing of optical elements which will later be used by human beings. The photo-voltaic cells are positioned so as to sense the light level or intensity reflected from the sphere wall opposite the detector, i.e., out of the direct path of reflection or transmission of the main beam to produce more accurate readings.

The apparatus and method may be used to test concave, convex or planar test samples as well as either first or second surface mirrors. The only limitation on concave and convex samples is that their radius of curvature must permit them to be tightly clamped between seals 50, 52 which typically means their radii of curvature must be equal to or larger than those of spheres 20, 30. Varying sizes and thicknesses of samples may be tested while the instrument and method provide highly accurate results because of the use of an optically stable, constant current, collimated light source as well as fixed optical geometry which need not be changed between tests. Moreover, the test pieces are easily and rapidly inserted without damage and the instrument need not be adjusted after each test with respect to a standard sample. The instrument and method provide reflectivity and transmission values corrected for the photopic human eye response making the unit and method highly effective for use in testing optical elements intended for later use by human beings.

While several forms of the invention have been shown and described, other forms will now be apparent to those skilled in the art. Therefore, it will be understood that the embodiments shown in the drawings and described above are merely for illustrative purposes and are not intended to limit the scope of the invention which is defined by the claims which follow.

The embodiments of the invention in which an exclusive property or privilege is claimed are defined as follows:

1. Apparatus for testing the light reflectivity and light transmission of an optical element or test sample such as a mirror or the like comprising:

first and second closed, hollow, light-integrating spheres aligned along a common axis, each sphere including a test aperture extending through its circumference, said test apertures being aligned with one another along said axis and intermediate the spheres when so aligned;

support means for supporting a test sample such as a mirror tightly against and between said spheres and immediately adjacent said test apertures and for clamping a test sample therebetween and sealing out ambient light from said spheres;

means for moving at least one of said spheres toward and away from the other for insertion of a test sample therebetween, said spheres being movable sufficiently close to one another so as to clamp said test sample tightly between said support means and seal out ambient light;

light source means for directing a beam of light at an angle to said axis through said first sphere, said test aperture in said first sphere, and against and at an angle other than normal to the surface of said test sample a predetermined area of which is exposed in said test aperture when said test sample is supported by said support means, said beam being directed so as to pass through both test apertures and into said second sphere in the absence of a test sample between said spheres;

photo-detection means for detecting the total amount of reflected light in said first sphere and the total amount of transmitted light in said second sphere; and means for separately indicating the total amounts of reflected and transmitted light, respectively, detected by said photo-detection means whereby the total light reflectivity and total light transmission of the said predetermined area of a test sample is simultaneously and instantaneously measured.

2. The apparatus of claim 1 wherein said support means include a pair of annular, pad-like, resilient rings, one ring extending around the test aperture on each sphere; said rings formed from material which blocks the passage of light therethrough.

3. The apparatus of claim 2 wherein said rings are formed from foam rubber.

4. The apparatus of claim 1 wherein said light beam is optically regulated and substantially collimated.

5. The apparatus of claim 4 wherein said light source means includes means for providing a source of constant electrical current and means for collimating said light beam.

6. The apparatus of claim 5 wherein said light source means includes means providing a beam of visible light substantially equal in spectral response to that of a light source classed as a standard illuminant A by the Commission Internationale de L'Eclairage; said means for collimating said beam including at least one lens and at least one adjustable iris for controlling the size of said light beam.

7. The apparatus of claim 1 wherein said photo-detection means include light-sensitive means in each sphere for detecting and sensing the amount of light present in each sphere and converting the detected amount into a quantity of electrical energy.

8. The apparatus of claim 7 wherein said light-sensitive means include one silicon, photo-voltaic cell positioned within an aperture extending through the circumference in each sphere such that the sensing surface of each of said cells is generally flush with the interior surface of its sphere.

9. The apparatus of claim 8 including a low-noise, high-gain, linear response amplifier and a visual readout display unit connected electrically to each of said silicon, photo-voltaic cells.

10. The apparatus of claim 1 wherein said photo-detection means include means for sensing all wavelengths of light visible to the human eye, said photo-detection means being matched and coupled to said indicating means so that the total amount of said visible wavelengths are indicated.

11. The apparatus of claim 1 wherein said means for moving one of said spheres include means for moving said second sphere toward and away from said first sphere.

12. The apparatus of claim 1 wherein said means for moving said one sphere include a fluid cylinder connected to said one sphere, means for mounting said one sphere for controlled sliding movement toward and away from said other sphere, and control means for operating said fluid cylinder.

13. The apparatus of claim 1 including means for supporting said first sphere vertically above said second sphere; said light source means being mounted on said first, upper sphere so as to direct said beam of light at an acute angle to the vertical; said one sphere being said second, lower sphere.

14. The apparatus of claim 1 wherein said indicating means include readout means for providing a visual readout of the total amounts of reflected and transmitted light detected by said photo detectors; said readout means including means for adjusting said reflectivity readout to be a percentage referenced to complete, total reflectivity set with a predetermined, known standard sample inserted and tested with said apparatus prior to the testing of any test sample and said transmission readout to be a percentage of the unimpeded light beam from said light source means in the absence of any test or standard sample.

15. Apparatus for testing the light reflectivity and light transmission of an optical element or test sample such as a mirror comprising:

a pair of closed, hollow, light-integrating means supported in axial alignment with one another along an axis for collecting, internally reflecting and averaging light present therewithin;

an aperture in each light-integrating means, said apertures being axially aligned along the axis of alignment of said light-integrating means and immediately adjacent one another between said light-integrating means;

means for supporting a test sample intermediate said light-integrating means and immediately adjacent said apertures in said light-integrating means and for clamping a test sample therebetween and sealing out ambient light from said light-integrating means;

means for controlled movement of one of said light-integrating means toward and away from the other for insertion, support, and clamping of a test sample between said light-integrating means such that the test sample is supported by said means for supporting a test sample and the ambient light is excluded from said light-integrating means;

light source means for directing an optically regulated, substantially collimated beam of light through said aligned apertures at an angle to the axis of alignment of said light-integrating means and apertures such that it will project through one of said light-integrating means and test apertures and will strike the surface of a test sample at an angle other than normal to said test sample surfact when said test sample is supported between said apertures; and means for simultaneously and substantially instantaneously detecting and indicating the total amount of light reflected in said one light-integrating means from a test sample when supported between said light-integrating means and apertures and the total amount of light transmitted through the test sample in the other light-integrating means when so supported.

16. The apparatus of claim 15 wherein said means for supporting a test sample include light seal means around each of said test apertures to prevent the entry into said light-integrating means of ambient light and to prevent the escape of light within said light-integrating means.

17. The apparatus of claim 15 wherein said detecting and integrating means include means for comparing the total amounts of reflected and transmitted light to known values set prior to said testing.

18. The apparatus of claim 15 wherein said light-integrating means each comprise a closed, hollow sphere having an optically white inside surface with a matte finish to provide diffuse internal reflection and an equal effect on the reflection of all visible wavelengths of light.

19. The apparatus of claim 18 wherein each of said spheres has an interior surface, an aperture adjacent which said sample is positioned and a light-sensitive detector, said one light-integrating means also including an aperture through which said beam of light is directed, said interior sphere surface areas being areas substantially larger than the sum of the aperture and detector areas in each respective sphere to provide high accuracy of the results from the apparatus.

20. A method for testing the light reflectivity and transmission of a test sample such as a mirror or other sheet of material comprising the steps of:

(1) directing a beam of light against the surface of a predetermined area on one side of a test sample at an angle other than normal to the surface of said area;

(2) simultaneously detecting the total amount of light reflected from said area of said test sample with a first light-integrating and sensing means on said one side of said test sample and the total amount of light transmitted through said area of said test sample with a second light-integrating and sensing means on the opposite side of said test sample while clamping the test sample tightly between said two light-integrating and sensing means, at least one of said two light-integrating and sensing means being movable toward and away from the other to effect clamping and sealing for excluding ambient light, said detection being performed while excluding said ambient light around said test sample from said light-integrating and sensing means, said total amount of reflected light including both diffusely and specularly reflected light; and (3) separately indicating on indicating means the respective total amounts of reflected and transmitted light detected.

21. The method of claim 20 including clamping said test sample and excluding said ambient light from said light-integrating and sensing means with light sealing means mounted around apertures in said light-integrating and sensing means to facilitate the accuracy of the method, said apertures defining said predetermined area of said test sample.

22. The method of claim 20 including directing an optically regulated, substantially collimated beam of light against said area of said test sample.

23. The method of claim 22 including generating said beam of light as substantially equal to the spectral response of a light source classed as a standard illuminant A by the Commission Internationale de L'Eclairage with a source of constant electric current.

24. The method of claim 23 including substantially instantaneously detecting the light present in each of said light-integrating and sensing means with a light-sensitive, photovoltaic detector cell in each light-integrating and sensing means.

25. The method of claim 20 including detecting and indicating the total amount of reflected and transmitted light from said test sample which is within the spectrum of wavelengths visible to the human eye so as to simulate the photopic response of the human eye.

26. The method of claim 20 wherein said clamping of said test sample tightly between said light-integrating and sensing means includes clamping said test sample immediately adjacent and intermediate a pair of adjacent, aligned test apertures through which the beam of light passes, one of said apertures being in each of said light-integrating and sensing means, while sealing the area around and between said apertures and test sample to prevent the entry of ambient light into said light-integrating and sensing means and the escape of reflected and transmitted light from said light-integrating and sensing means.

27. The method of claim 20 wherein said indicating step includes separately comparing the total amounts of reflected and transmitted light detected with said light-integrating and sensing means to known, pre-set values determined prior to said testing.

28. The method of claim 20 including detecting the total amounts of reflected and transmitted light at a location within said light-integrating and sensing means out of direct alignment with the paths of the principal reflected and transmitted beams of light from said area of the test sample.

29. The method of claim 20 including separately detecting said total amount of reflected and total amount of transmitted light from said area of the test sample with separate, axially aligned, light-integrating spheres each including a light-sensitive, photo-voltaic cell, one sphere positioned on each side of said test sample; said beam of light being directed from one of said spheres.

* * * * *

UNITED STATES PATENT AND TRADEMARK OFFICE
CERTIFICATE OF CORRECTION

PATENT NO. : 4,120,582

DATED : October 17, 1978

INVENTOR(S) : Martin De Vries, Harold A. Fitzgerald II

It is certified that error appears in the above-identified patent and that said Letters Patent are hereby corrected as shown below:

Column 1, line 36:
"representation" should be --representational--

Column 1, line 60:
"of" should be --through--

Column 1, line 61:
delete "similar" and insert therefor --consistent with--

Column 2, line 61:
"element" should be --elements--

Column 5, line 28:
"anotheer" should be --another--

Column 8, line 41:
"the" should be --an--

UNITED STATES PATENT AND TRADEMARK OFFICE
CERTIFICATE OF CORRECTION

PATENT NO. : 4,120,582
DATED : October 17, 1978
INVENTOR(S) : Martin De Vries, Harold A. Fitzgerald II It is certified that error appears in the above–identified patent and that said Letters Patent are hereby corrected as shown below:

Column 8, line 26:
after "ments" insert --, except for the light bulb voltage adjustment,--

Column 8, line 65:
delete "is switched on and"

Signed and Sealed this

First Day of July 1980

[SEAL]

Attest:

SIDNEY A. DIAMOND

Attesting Officer  Commissioner of Patents and Trademarks